United States Patent
Knapp

(10) Patent No.: US 6,546,289 B2
(45) Date of Patent: Apr. 8, 2003

(54) TERMINAL DESIGN WITH ANGLED COLLAR

(75) Inventor: Christopher P. Knapp, Ham Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 82 days.

(21) Appl. No.: 09/843,441

(22) Filed: Apr. 26, 2001

(65) Prior Publication Data

US 2002/0161413 A1 Oct. 31, 2002

(51) Int. Cl.[7] .............................................. A61N 1/375
(52) U.S. Cl. ........................................ 607/37; 439/909
(58) Field of Search ...................... 607/37, 122, 123, 607/38; 439/909

(56) References Cited

U.S. PATENT DOCUMENTS

| | | | | |
|---|---|---|---|---|
| 4,105,037 A | * | 8/1978 | Richter et al. ................. | 607/37 |
| 5,233,987 A | * | 8/1993 | Fabian et al. ................. | 600/587 |
| 5,679,026 A | * | 10/1997 | Fain et al. .................... | 439/651 |
| 5,906,634 A | * | 5/1999 | Flynn et al. ................... | 607/37 |
| 6,285,905 B1 | * | 9/2001 | Chiang et al. ................. | 128/907 |
| 6,409,531 B1 | * | 6/2002 | Millard ........................ | 439/289 |

* cited by examiner

*Primary Examiner*—Kennedy Schaetzle
(74) *Attorney, Agent, or Firm*—Thomas J. Nikolai; Nikolai & Mersereau, P.A.

(57) ABSTRACT

An implantable medical lead including an angled collar located adjacent to or integral with the proximal connector assembly is provided. The angled collar provides a area having enhance rigidity to allow insertion of the connector assembly without kinking or otherwise bending the conductors within the lead body. The angled collar comprises a bend adjacent the proximal end of the lead having a reinforcing layer disposed about the lead body. The angled collar may include a textured surface to reduce the likelihood of the users finger or fingers sliding off of the angled collar during insertion.

10 Claims, 4 Drawing Sheets

TERMINAL DESIGN WITH ANGLED COLLAR

BACKGROUND OF THE INVENTION

1. Field of the Invention

The present invention relates to implantable medical tissue stimulating devices and, more particularly, to implantable leads for connection to such medical devices.

2. Background of the Related Art

Implantable leads are used in conjunction with a variety of medical devices to transmit electrical signals to the devices from a target location in the body and/or stimuli from the devices to the target location. The implantable leads are typically manufactured as separate components of a tissue stimulating system rather than being a part of the tissue stimulator itself. Therefore, the lead typically requires an interconnection to the implantable medical device with which it is used. This interconnection includes a connector assembly that is located on the proximal end of an elongated lead body. The connector is adapted to be inserted into a header port in the medical tissue stimulating device.

Currently, electrical connector assemblies on leads used to connect to cardiac pacemakers generally correspond to the IS-1 connector standard. Alternatively, connector assemblies used to connect to implantable defibrillators and, particularly, those used in conjunction with high energy cardioversion and defibrillation electrodes may correspond to the DF-1 connector standard.

In addition to conforming to the various standards, the connector assemblies typically include one or more sealing rings to seal the header ports. The seals are configured to prevent fluid entry into the medical device and to form seal between the individual electrical contacts on the connector assembly when the connector assembly is seated in the header port. The seals are typically tightly squeezed between the connector assembly and the header port to form the seal. The compression of the seals increases the force required to insert the connector assembly into the header port. In addition, the frictional resistance further increases the force necessary for insertion. In use, the force necessary for insertion is applied to the proximal end of the lead body adjacent to the connector assembly. Due to the flexibility of the lead body, it has a tendency to buckle or kink during insertion of the connector into its socket of the device's header. The buckling or kinking can damage the lead's conductors that may result in the lead failing and thus, having to be abandoned or explanted. Alternatively, the lead body may be bent so that force may be applied to the relatively rigid connector assembly's distal end. Again, the bending of the conductors and application of a compressing force has a tendency to kink and break the conductors and/or insulation within the lead body resulting in the need to replace the whole lead. Therefore, a need exists for a connector assembly that permits the application of requisite force for seating the lead connector without the buckling or kinking of the lead's conductors.

Current leads typically employ one of two general mechanisms to assist inserting the lead's connector assembly into the header port of the medical device. The first mechanism consists of a coil or tube, mounted within the lead body and which extends distally from the proximal end of the lead body. This coil or tube provides the proximal end of the lead body with increased column strength and rigidity to assist insertion of the connector assembly into the header port. The coil or tube provides rigidity to the adjacent lead body but the coil or tube does not provide a gripping surface nor does the coil or tube address the innate tendency for a medical professional to push on the end of the coil or tube by bending the lead body at the distal end of the coil or tube and pushing with the thumb, an approach which tends to damage the conductors. The second mechanism consists of a stress relief sleeve mounted over a proximal portion of the lead body. The stress relief sleeve provides a grip which the physician may grasp when inserting the lead. Although the stress relief sleeve may reduce the amount of buckling or kinking, the sleeve only provides structure for gripping the lead body between two fingers and again does not address the innate tendency of a user to want to push with his/her thumb. Therefore, a need exists for a design for the proximal end of a lead that allows for users to push the connector assembly into the header port with his/her thumbs without increasing the risk of damaging the conductors.

SUMMARY OF THE INVENTION

The present invention provides a medical lead providing an angled collar configured to aid the user in the insertion of the connector region into the header port without damaging the lead by providing a surface on which to press and thereby apply a force along the longitudinal axis of the connector. The medical lead, in accordance with the invention, comprises an insulating lead body having a proximal end and a distal end and at least one conductor extending therebetween, and having a male connector member attached to the conductor of the lead body at the proximal end thereof. An angled collar is attached to the lead body adjacent the connector assembly. The angled collar is configured to provide a surface that when pressed, causes a force to be applied along a longitudinal axis of the connector assembly to facilitate insertion of the connector assembly into a female header port.

DETAILED DESCRIPTION OF THE INVENTION

The present invention is applicable to a variety of medical devices utilizing implantable leads. The invention is described generally in the context of a cardiac pacing lead used with implantable cardiac rhythm management devices for illustrative purposes only. The appended claims are not intended to be limited to any specific end use, example or embodiment described in this specification. Those skilled in the art will understand that the present invention may be used in a wide variety of medical applications including, but not limited to, neurostimulation, pacing and defibrillation. Further, the numbers are repeated throughout the figures where the individual elements are substantially identical to one another.

Figure 1:
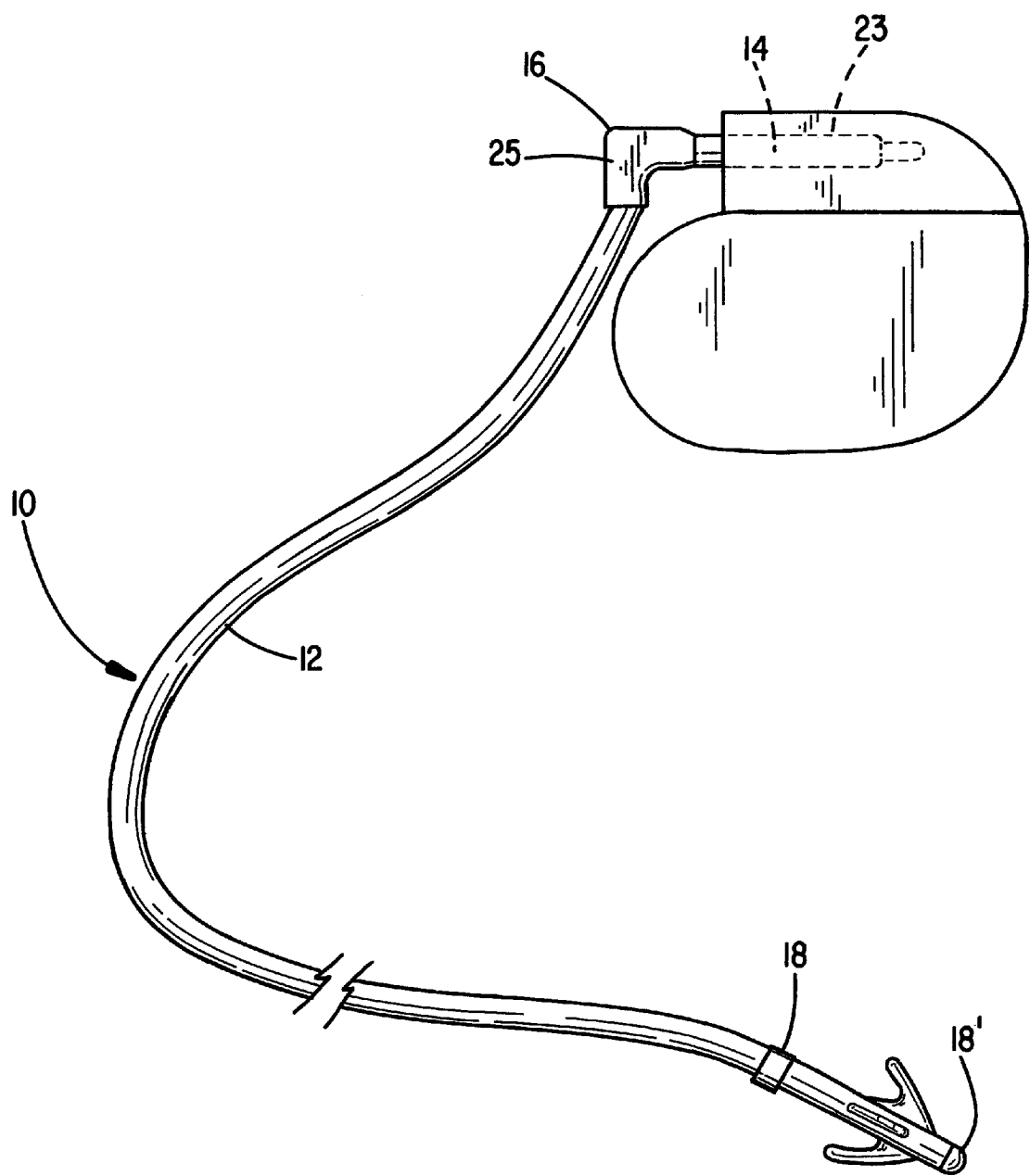
FIG. 1 illustrates a perspective view of a medical lead in accordance with the present invention attached to a conventional cardiac rhythm management device.

Referring first to FIG. 1, it illustrates a perspective view of a medical lead 10 in accordance with the present invention. Lead 10 includes an elongated, flexible lead body 12 having a connector assembly 14 attached at its proximal end. An angled collar 16 surrounds and is attached to the proximal end of lead body 12 immediately distal of connector assembly 14, and one or more stimulating/sensing electrodes are attached near or at the distal end of lead body 12. Further, lead body 12 may be provided with a lumen 20, shown in FIGS. 2 and 3, to permit insertion of a stylet during implantation or to permit drug delivery.

Lead body 12 further includes one or more insulated conductors 22 extending between the electrodes 18–18' and the connector 14 The insulator is typically flexible to permit lead 12 to be inserted intravenously to a target location within the patient.

Connector assembly 14 includes one or more contacts depending on whether it is a monopolar or a bipolar lead, and a connector body having sufficient rigidity to permit insertion of the connector assembly into the conventional header port 23 on the can or housing of the pulse generator. The conductors 22 electrically connect the electrical contacts disposed longitudinally on connector assembly 14 with the electrodes and/or sensors at the distal end of lead body 12.

Angled collar 16 forms an angle in lead body 12 or on connector assembly 14 to allow the user to apply a force along the longitudinal axis of the connector pin during insertion of connector assembly 14 into the header port 23. Typically, angled collar 16 is configured to enable a user to apply the necessary force with the user's thumb or other finger pushing on the surface 25. Surface 25 may be textured to provide increased friction between the user's thumb or finger. Angled collar 16 may be formed from a biocompatible polymer or other biocompatible material. The material used is selected to have sufficient rigidity to withstand the force of insertion without buckling or bending. Polyetheretherkeyton (PEEK), polyurethane and tecothane have been found to be suitable plastics for the collar 16.

Angled collar 16 preferably comprises a rigid angled band placed about lead body 12 adjacent to connector assembly 14. Alternatively, angled collar 16 may be attached to the proximal end of lead body 12 and to the distal end of connector assembly 14. While the drawings illustrate angled collars having 90° bends, other angles, preferably in a range from about 60° to 150° can be used.

In the preferred embodiment, angled collar 16 includes one or more conductors molded into the collar or passing through the lumen formed in the collar to electrically connect the conductors 22 of lead body 12 with the electrical contacts of connector assembly 14. In yet another embodiment, angled collar 16 is integral with the distal end of connector assembly 14.

Figure 2:
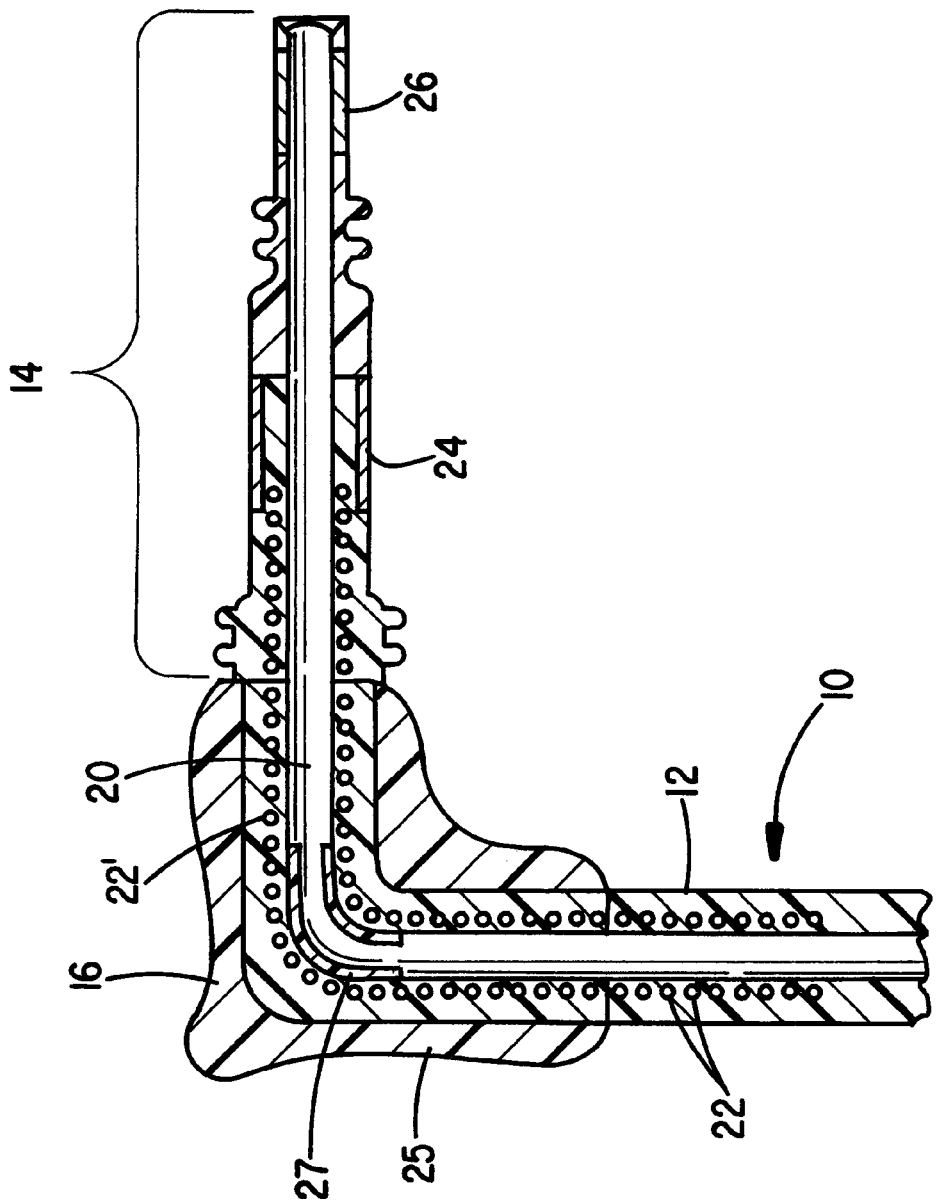
FIG. 2 illustrates a sectional view of the proximal end portion of the lead of FIG. 1 showing an angled collar in accordance with the present invention.

FIG. 2 illustrates a partial sectional view of the proximal end portion of and incorporating the present invention. Lead 10 includes a stylet receiving lumen 20 extending from the proximal end of connector assembly 14 through the bend in lead body 12 at angled collar 16 and down to the distal end of the lead. Angled collar 16, as shown in FIG. 2, is secured around the proximal end of lead body 12. Conductors 22 are spirally wound within lead body 12 around lumen 20. Conductors 22 electrically connected to first contact 24 and second contact 26 of connector assembly 14. To prevent penetration of a stiffening stylet through the plastic at the point of the angled bend, a reinforcing tube 27 can be employed within the lumen 20.

Angled collar 16 is secured about lead body 12 to prevent the buckling or kinking of conductors 22 during insertion of connector assembly 14 into the header of a medical device as the medical professional applies thumb pressure to the surface 25 of the angled collar. As shown in FIG. 2, the proximal end of the angled collar 16 abuts the distal end of connector assembly 14. Angled collar 16 may be positioned more distal along lead 16 to permit some flexibility between the angled collar and the connector assembly while still preventing buckling or kinking.

Figure 3:
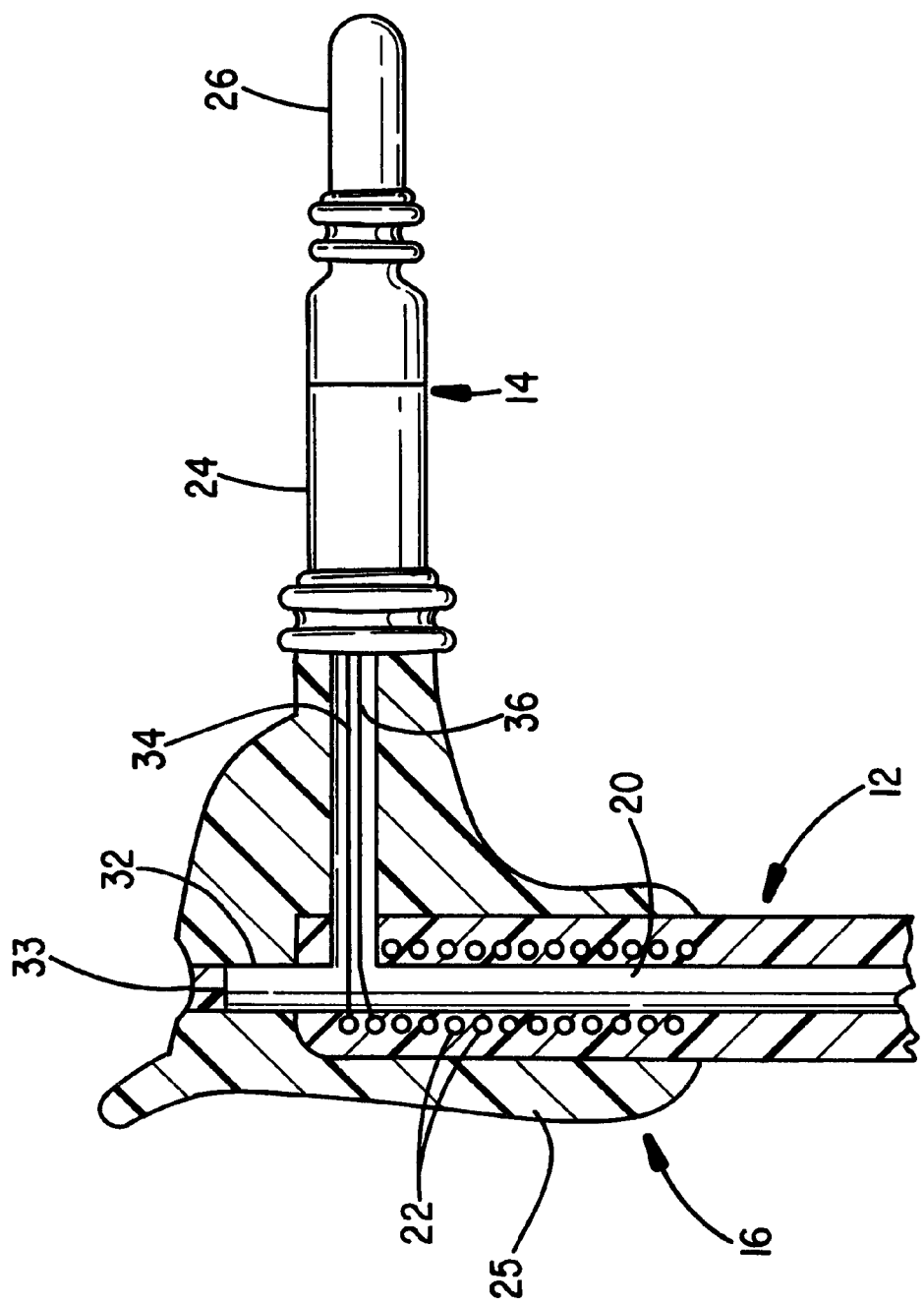
FIG. 3 illustrates a sectional view of an alternative embodiment of an angled collar in accordance with the present invention.

FIG. 3 illustrates a partial sectional view of the proximal end of another embodiment of lead 10. Angled collar 16, as shown in FIG. 3, is integral with connector assembly 14. Stylet receiving lumen 20 is continuous and collinear with a passage 32 at the distal end of connector assembly 14 adjacent the angled collar 16 so as not to require a stylet to bend as in the embodiment of FIG. 2. A self-sealing plug 33 allows penetration of the stylet but prevents ingress of the body fluids when the stylet is withdrawn following implant.

At least one wound conductor 22 from lead body 12 is electrically connected to first contact 24 and/or second contact 26 of connector assembly 14. As shown in FIG. 3, a first connecting wire 34 electrically connects first contact 24 to a spiral wound conductor 22 in the lead body and a second connecting wire 36 electrically connects second contact 26 to another spiral wound conductor 22. Alternatively, conductors 22 may be drawn from lead body 12 during manufacture and extended through angled collar 16 and connector assembly 14 to electrically contact first contact 24 and/or second contact 26.

Figure 4:
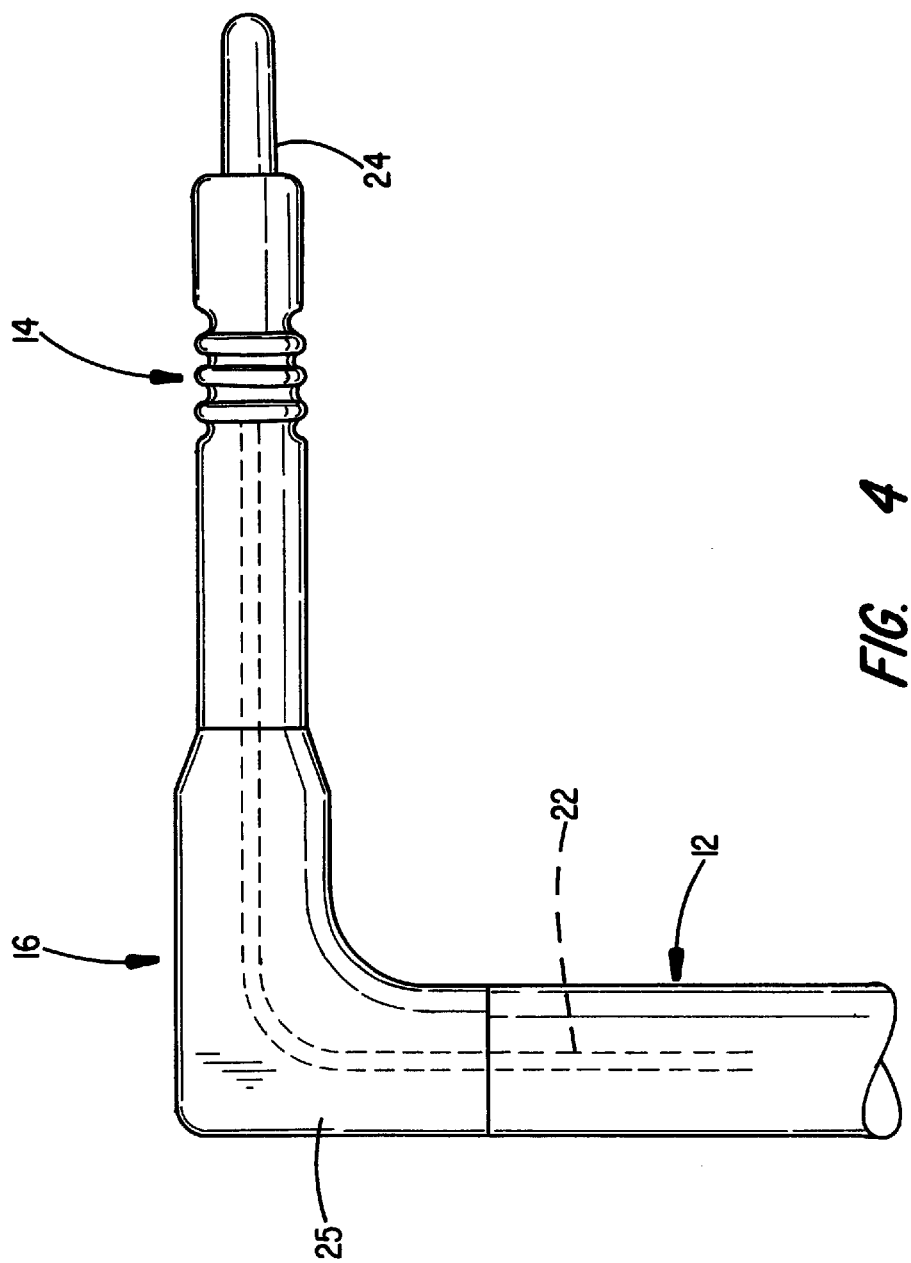
FIG. 4 illustrates a sectional view of yet another embodiment of an angled collar in accordance with the present invention.

FIG. 4 illustrates a partial sectional view of the proximal end of yet another embodiment of a cardiac stimulating lead 10. Angled collar 16, as shown in FIG. 4, is an independent element secured between the proximal end of lead body 12 and the distal end of connector assembly 14. Electrical contact 24 of connector assembly 14 is electrically connected to at least one conductor 22, shown as a cable conductor of the type used in the fabrication of defibrillating leads. FIG. 4 illustrates the connection of cable conductor 22 to electrical contact 24 by extending conductor 22 through angled collar 16 and connector assembly 14 to form the electrical contact with electrical contact 24. Alternatively, a connecting wire or wires could be molded in or inserted through a lumen into connector assembly 14 and angled collar 16 to electrically connect electrical contact 14 with conductor 22.

The embodiments of the angled collar shown in FIGS. 2 and 3 are compatible with lead connectors meeting International Standards IS-1 and IS-2 while the embodiment of FIG. 4 is applicable to the DF-1 standard. It is to be understood, however, that the present invention is applicable to almost any terminal connector design.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. A medical lead, comprising:
    an insulating lead body having a proximal end and a distal end and at least one conductor extending therebetween;

a male connector assembly attached to the at least one conductor of the lead body at the proximal end of the lead body;

an angled collar attached to the lead body adjacent the connector assembly, the angled collar including a passageway comprising two lumen segments that intersect with one another at a predetermined angle, the lead body being contained within at least one of the lumen segments in said passageway, the angled collar being configured to provide a surface that when pressed causes a force to be applied along a longitudinal axis of the connector assembly to facilitate insertion of the connector assembly into a female header port; and a stylet receiving lumen formed in the lead body extending from the proximal end to the distal end.

2. The medical lead of claim 1 wherein the predetermined angle is in a range of from 60° to 150°.

3. The medical lead of claim 1 wherein the predetermined angle is about 90°.

4. The medical lead of claim 1 wherein the lead body is contained in both of the two lumen segments.

5. The medical lead of claim 1 wherein the lead body is contained in one lumen segment of the passageway and a conductor link joining the at least one conductor of the lead body to the male connector assembly is contained in the other lumen segment of the passageway.

6. The medical lead of claim 5 wherein the connector assembly comprises an insulating cylindrical member having at least one electrical contact on the surface thereof and the conductor link joins the at least one conductor of the lead body to the at least one electrical contact.

7. The medical lead of claim 1 wherein the angled collar includes a reinforcing element proximate the intersection of the two lumen segments to steer a stylet inserted through the stylet receiving lumen through the predetermined angle without penetrating through a wall of the insulating lead body defining the stylet receiving lumen.

8. The medical lead of claim 7 wherein the connector assembly comprises a tubular structure having at least one electrical contact on a surface thereof, the tubular structure including a lumen that is aligned with one of the lumen segments of the angled collar.

9. The medical lead of claim 1 wherein the angled collar includes a stylet receiving lumen that is collinear with the stylet receiving lumen of the lead body when the lead body is disposed in the at least one lumen segment.

10. The medical lead of claim 9 and further including a self-closing penetrable seal member contained in the stylet receiving lumen of the angled collar.

* * * * *